(12) United States Patent
Doak et al.

(10) Patent No.: US 7,201,064 B2
(45) Date of Patent: Apr. 10, 2007

(54) PANEL BENDING MACHINE

(75) Inventors: Jody Doak, Jefferson, GA (US); Shannon D. Guffey, Philadelphia, PA (US)

(73) Assignee: Huber Engineered Woods LLC, Charlotte, NC (US)

( * ) Notice: Subject to any disclaimer, the term of this patent is extended or adjusted under 35 U.S.C. 154(b) by 53 days.

(21) Appl. No.: 11/088,927

(22) Filed: Mar. 25, 2005

(65) Prior Publication Data

US 2006/0213281 A1    Sep. 28, 2006

(51) Int. Cl.
*G01N 3/20* (2006.01)
*G01N 3/00* (2006.01)

(52) U.S. Cl. .......................................... 73/849; 73/788

(58) Field of Classification Search ................. 73/849, 73/856

See application file for complete search history.

(56) References Cited

U.S. PATENT DOCUMENTS

| | | | |
|---|---|---|---|
| 3,286,516 A | 11/1966 | Post | |
| 4,589,288 A | 5/1986 | Porter et al. | |
| 4,648,285 A | 3/1987 | Carson | |
| 4,708,020 A | 11/1987 | Lau et al. | |
| 4,792,737 A * | 12/1988 | Goff et al. | 318/615 |
| 4,838,085 A * | 6/1989 | Pellerin et al. | 73/597 |
| 5,060,516 A * | 10/1991 | Lau et al. | 73/602 |
| 5,491,372 A * | 2/1996 | Erhart | 310/80 |
| 5,503,024 A * | 4/1996 | Bechtel et al. | 73/852 |
| 5,557,154 A | 9/1996 | Erhart | |
| 5,804,738 A | 9/1998 | Bach et al. | |
| 5,899,103 A * | 5/1999 | Ooenoki et al. | 72/31.1 |
| 5,955,853 A * | 9/1999 | Lander | 318/439 |
| 6,053,052 A * | 4/2000 | Starostovic | 73/851 |
| 6,055,867 A | 5/2000 | Dunne et al. | |
| 6,381,546 B1 * | 4/2002 | Starostovic | 702/36 |
| 6,505,129 B2 * | 1/2003 | Starostovic et al. | 702/36 |
| 6,712,907 B1 | 3/2004 | Pratt et al. | |
| 6,756,707 B2 * | 6/2004 | Hochhalter et al. | 310/20 |
| 6,806,595 B2 | 10/2004 | Quarre | |
| 2003/0192385 A1 | 10/2003 | Uhlik et al. | |
| 2006/0017032 A1 * | 1/2006 | DeWall et al. | 251/129.11 |

OTHER PUBLICATIONS

U.S. Department of Commerce Technology Administration. National Institute of Standards and Technology. Voluntary Product Standard PS 1-95: Construction and Industrial Plywood. Natl. Inst. Stand. Technol. Prod. Stan. 1-95, 48 pages. Mar. 1996. http://ts.nist.gov/ts/htdocs/210/sccg/ps1-95.pdf, obtained Jul. 10, 2006.*

(Continued)

*Primary Examiner*—Edward Lefkowitz
*Assistant Examiner*—Punam Patel
(74) *Attorney, Agent, or Firm*—Ramon Hoch; Carlos Nieves

(57) ABSTRACT

A panel testing device, and a method of its use, for flexing and measuring mechanical properties of a panel are provided comprising a panel bending assembly operable to engage a panel and impart a bending force on the engaged panel, and a linear actuator having an output shaft coupled to the panel bending assembly, wherein the output shaft is operable to be movable relative to the panel bending assembly continuously at a constant rate of linear motion regardless of the torque force resisting such motion at the panel testing assembly.

21 Claims, 10 Drawing Sheets

OTHER PUBLICATIONS

"Standard Methods of Testing Structural Panels in Flexure," ASTM Std. Designation D 3043-95, Sep. 1995, pp. 1-11, ASTM International, West Conshohocken PA, U.S.A.

Form and Style for ASTM Standards, "A21. Precision and Bias (Mandatory)," Sep. 2004, A-13 through A-15, ASTM International, West Conshohocken PA, U.S.A.

* cited by examiner

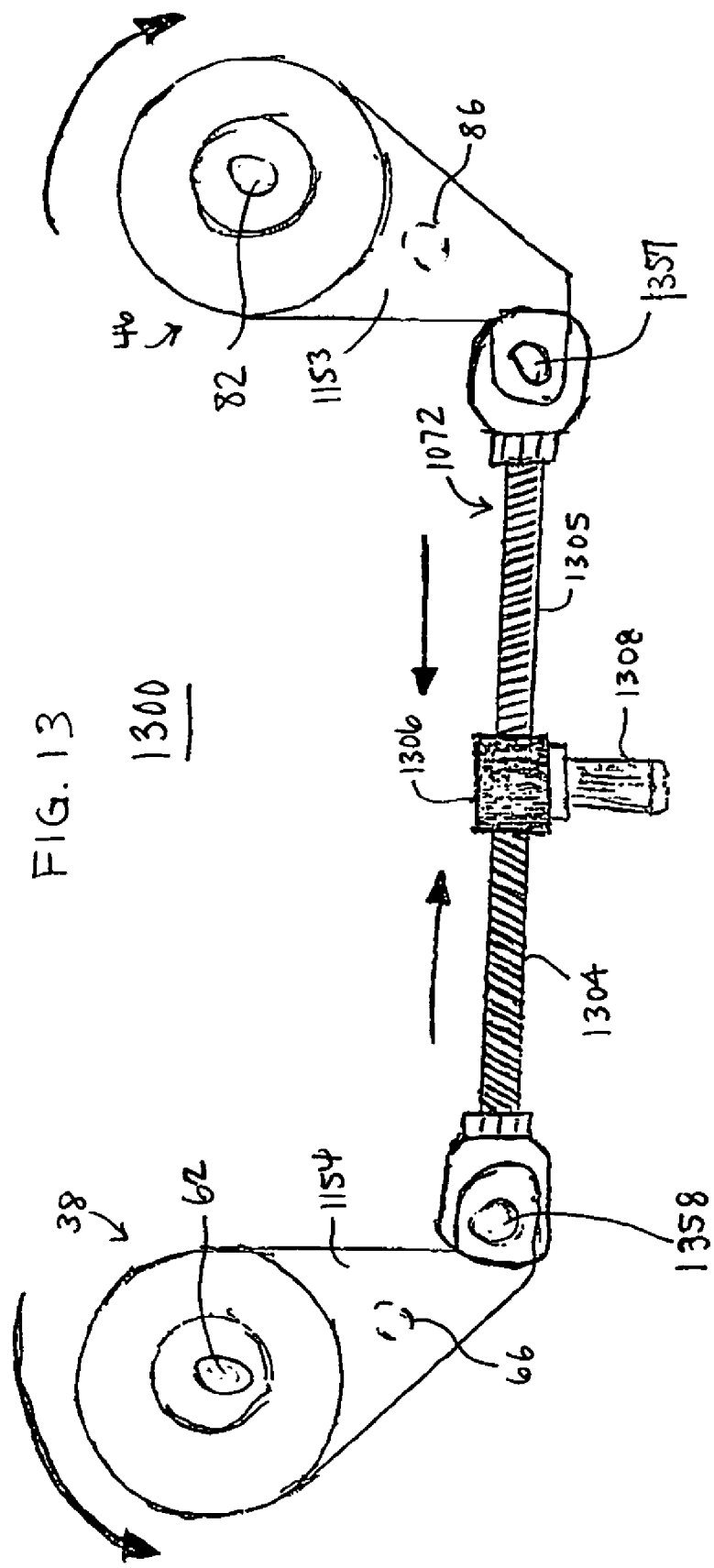

PANEL BENDING MACHINE

FIELD OF THE INVENTION

This invention relates to devices for testing mechanical properties of panel materials, and methods of use thereof.

BACKGROUND OF THE INVENTION

An increasing demand exists for pre-fabricated structural panel materials, such as plywood, wafer board, oriented strand board, plaster board, composites of veneer and of wood-based layers, and so forth. These structural materials are heavily used, for instance, in the construction and manufacturing industries. Suppliers and users of these products often need to know their flexural properties, e.g., elastic and strength properties, to assist them in making a proper material selection. Specimen or control panels cut from large panels or pulled from a given production lot are tested to determine the flexural properties of the panel material. It is imperative that the testing arrangement used for these tests yields accurate, reliable and repeatable results to increase confidence that the control panel results are representative of the entire production lot.

Devices for performing flexural tests on sheet or strip materials are known which are configured to apply a controlled load to a testing panel while concurrently recording the deflection of the test panel as the load is applied. For instance, for a known test panel geometry, load and deflection data can be measured on such devices during a test cycle. The panels are flexed and deflection measured to determine panel modulus and stiffness, and flexure is continued until rupture to determine the panel strength.

U.S. Pat. No. 3,286,516 describes a machine for performing flexural test on panels comprising a force producing means connected to a cable and pulley system which converts the force to opposite torques acting about parallel axes, in which loading frames are mounted on both torque axes for applying torques to a flexure specimen. A torque measurement apparatus is mounted on one of the torque axes, and the torque axes are supported on carriages and tracks for free rotation and lateral movement. Among other drawbacks, the cables can stretch, and the device can get out of calibration as the cables stretch, requiring their replacement. Also, depending on the panel strength needed, different sizes of cables may need to be installed on the device to test different thicknesses of test panels.

U.S. Patent Application Publication No. 2003/0192385 A1 describes a panel bending and testing device in which the drive system is powered by pneumatics and hydraulics.

A panel testing device which provides accurate and repeatable results with reduced parts maintenance requirements would be desired by those skilled in the art.

SUMMARY OF THE INVENTION

The above needs are met and other advantages and benefits are achieved by the present invention in which a panel testing device for flexing and measuring mechanical properties of a panel is provided comprising a panel bending assembly operable to engage a panel and impart a bending force on the engaged panel, and includes a linear actuator having an output shaft coupled to the panel bending assembly where movement of the output shaft correspondingly changes the bending force applied to a test panel engaged by the panel bending assembly, and wherein the output shaft is operable to be movable relative to the panel bending assembly continuously at a constant rate of linear motion regardless of the torque force resisting such motion at the panel testing assembly. A position feedback assembly is included operable to generate signals corresponding to the position and velocity of the output shaft of the linear actuator, and a deflection measurement assembly included is operable to measure a deflection of the panel during a testing cycle. A control system also included which is operable to communicate with the linear actuator, position feedback assembly, and the deflection measurement assembly for controlled operation thereof, including receiving first signals from the deflection measurement assembly that correspond to the deflection of the panel and second signals from the position feedback assembly that correspond to the position and velocity of the output shaft of the linear actuator, wherein the control system is adapted to adjust the velocity of the output shaft in response to the second signals to produce a constant rate of linear motion thereof. Unlike some prior systems, the output shaft of the linear actuator delivers a continuous actuation stroke during and throughout a given panel test cycle without pausing or hesitating, especially during the beginning of a test cycle where such undesired phenomenon has been observed to be more prone to occur in prior systems. Not only is the actuation stroke continuous, but additionally the output shaft moves at a constant rate of linear motion during a test cycle. Testing results are more reliable as they are not corrupted by discontinuities in actuator movement and/or non-constant velocities of actuation. For purposes herein, a "constant rate of linear motion" means the velocity of the output shaft as measured during a panel testing cycle remains within ±4.0% of a target value. It will be appreciated that the velocity of the actuator output shaft velocity may be measured directly or indirectly via related actuator drive components (as will more apparent from descriptions provided infra). In further embodiments that rate of linear motion of the output shaft of the actuator remains within ±1.0%, particularly within ±0.5%, and more particularly within ±0.2%, during a panel testing cycle.

The present investigators have recognized and filled a need for a flexure test system for testing mechanical properties of pre-fabricated structural panel materials which can provide a continuous and constant rate of actuation via the automated drive system used to deliver a bending force at the panel testing assembly during a test cycle regardless of the torque force at the panel bending assemblies resisting such motion. In a preferred embodiment, a drive assembly comprises a linear actuator which is mechanically coupled to the panel bending assembly and driven by a power transmission means with real-time monitoring and adjustment of the output shaft's position and velocity making it possible to translate the actuator output shaft continuously at a constant rate of linear motion and bend a test panel in a highly controlled manner. This allows more accurate and repeatable mechanical property determinations to be made on test panels. The drive assembly, among other contributed advantages, eliminates error found to be associated with use of a hydraulic drive system in panel testing devices, which in turn provides more accurate, more repeatable, and less variable results. With the reduction in error, not only does repeatability improve, but average values increased significantly. For instance, a panel test device incorporating the above-indicated drive assembly instead of a hydraulic drive system has been observed to have repeatability error reduced on average by 25%, and in some cases reduced by 50%, by comparison, all other variables generally equal. For purposes herein, "repeatability" has the same meaning as "precision" as defined in the *Form and Style for ASTM Stan-*

*dards*, ASTM International, West Conshohocken Pa., A21.2.1, September 2004. In addition, average stiffness values have been observed to increase by approximately 8%. The observed slight increase in the average value is correlated to the decrease in variation. In this instance, the decrease in variation results in a slight increase in the slope of the line used to calculate stiffness of the panel being tested. These improvements can translate into large savings in manufacturing as production can require fewer raw materials to meet specifications. In addition, the panel testing machine of the present invention is relatively easy to maintain and operate for numerous testing cycles while maintaining a high degree of accuracy and reliability in the test results.

In a particular embodiment, the output shaft of the linear actuator is coupled to the panel bending assembly via a mechanical linkage. The mechanical linkage may comprise a pair of bent levers that each are mechanically and pivotally connected at one end thereof to a distal end of the output shaft of the linear actuator, and which include a pivot at a bent point or elbow before making a connection at the opposite end thereof with an arm assembly of the panel bending assembly. The mechanical linkage is used to change the direction of force of the output shaft by converting its linear motion to rotary motion. In another particular embodiment, the linear actuator comprises a roller screw and rolling elements operably connected to the power source and the output shaft. The linear actuator may comprise multiple threaded helical rollers assembled in a planetary arrangement around a portion of the output shaft comprising a threaded shaft adapted to move the output shaft, wherein the linear actuator converts rotary motion into linear movement of the threaded shaft. A power source operable to deliver constant power transmission to the linear actuator is used, such as a closed loop D.C. servomotor, a D.C. servomotor, a D.C. stepper motor, or a constant torque A.C. motor, and the like. The position feedback assembly may be selected, e.g., from a resolver, a linear position feedback sensor, or an encoder, etc., which can be internally mounted within the linear actuator at a location where the output shaft thereof translates during a testing cycle or can be mounted completely external to the actuator. The deflection measurement assembly may comprise an end portion supporting a deflection sensor, wherein the end portion being movable between a non-testing position where the sensor is out of contact with the panel and a test position where the sensor is in contact with the panel when the deflection sensor is in the test position operable to measure a deflection of the panel.

In a more particular embodiment, the panel testing device further comprises a frame and the panel bending assembly further comprises a first arm assembly pivotally mounted to the frame and including a first arm engageable with a first major face of the panel and having a generally perpendicular first axis, and second arm engageable with a second major face of the panel and having a generally perpendicular second axis that is spaced from and substantially parallel to the first axis, and a second arm assembly pivotally mounted to the frame and including a third arm engageable with the first major face and having a generally perpendicular third axis, and a fourth arm engageable with the second major face and having a generally perpendicular fourth axis which is spaced from and substantially parallel to the third axis. The first and third arms are controllably pivotable in opposing rotational directions to bend the panel via external mounts made thereto with the linear actuator. The linear actuator is operable to simultaneously pivot the first and third arms in opposite rotational directions at the same rotational speeds. The output shaft of the linear actuator may be coupled to the first and third arms via a mechanical linkage. Alternatively, the linear actuator is coupled via its output shaft to the first and third arms of the panel bending assembly via direct attachment thereto. In a further embodiment, a load sensor can be provided which engages at least one of the arms, wherein the load sensor measures at least a portion of a bending load that is applied to the panel as the arm assembly pivots.

In another embodiment, the present invention provides a method for testing a panel of material, comprising (A) providing a panel testing device as indicated above; (B) inserting a test panel into the testing device; (C) powering the linear actuator effective to impart a bending force on opposite ends of the test panel; (D) moving the output shaft at a constant rate of linear motion along a plurality of different axial positions relative to the panel bending assembly; and (E) operating, during step (D), the deflection measurement assembly to detect the deflection of the test panel at said different axial positions and outputting signals corresponding to the amount of deflection thereof at the different axial positions of the output shaft of linear actuator. In one embodiment, the method can be used to measure panel deflection in accordance with ASTM D 3043-95, method C.

Other features and advantages of the invention will become apparent to those skilled in the art upon review of the following detailed description and drawings.

BRIEF DESCRIPTION OF THE DRAWINGS

FIG. 13 is a top plan view of an actuation system for the panel testing device of FIG. 1 according to yet another embodiment of the invention.

The figures and elements therein are not necessarily drawn to scale. Similarly numbered elements in different figures represent like features unless indicated otherwise.

DETAILED DESCRIPTION OF THE PREFERRED EMBODIMENTS

Figure 1:
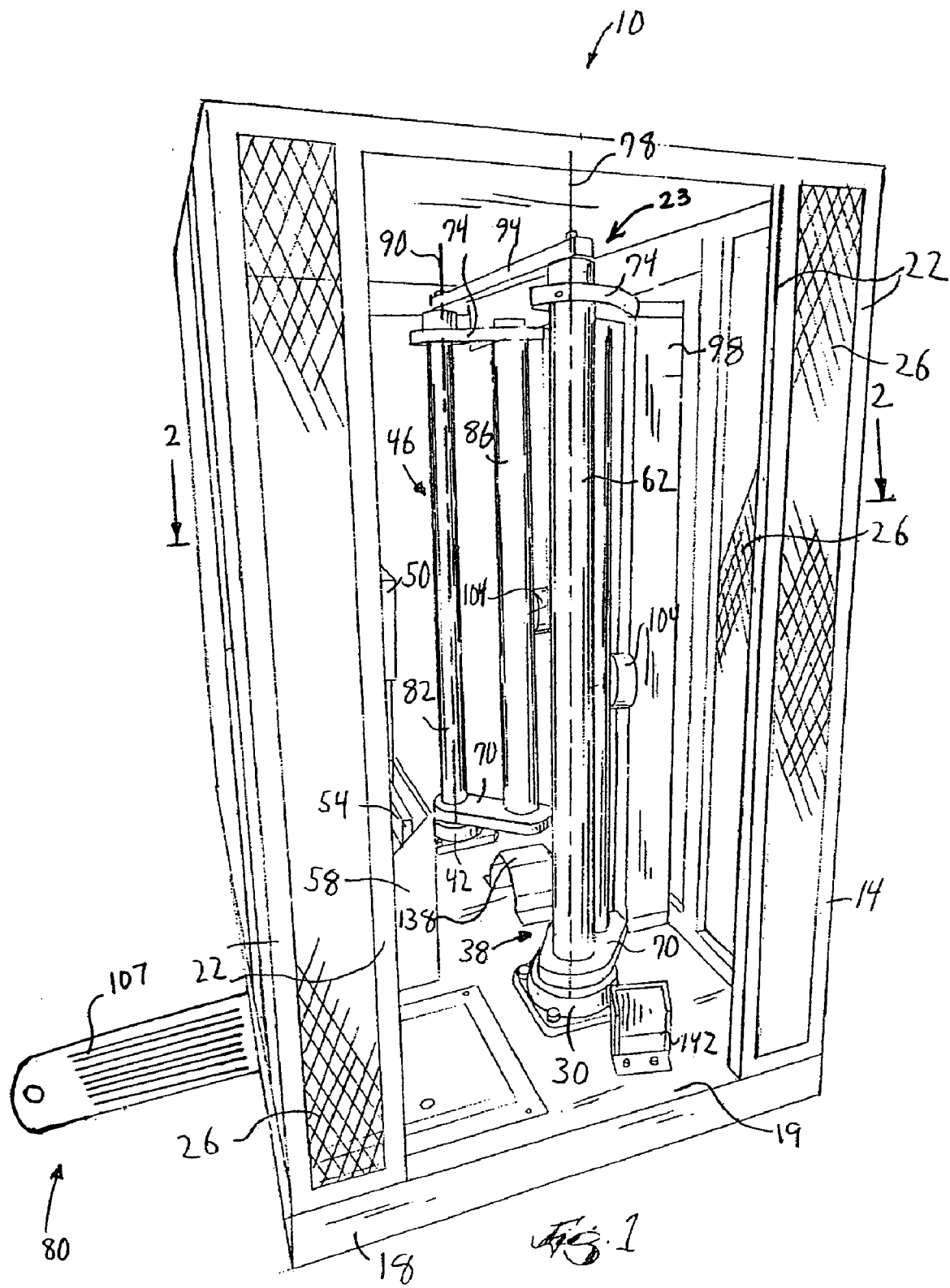
FIG. 1 is a perspective view of a panel testing according to an embodiment of the invention.

Preferred embodiments of the invention are described below by referring to the drawings. Referring to FIG. 1, a panel testing device 100 is shown which includes of a metal cage (frame) 14 with two sets of two arm assemblies 38, 46 that rotate and flex a panel to determine mechanical properties of the panel, such as find deflection between two loads (stiffness) and failure at ultimate load (strength).

When determining mechanical properties of test panels according to standard methods of testing in flexure, such as in accordance with ASTM D 3043-95, method C, in which load deflection curves can be measured and used to determine bending stiffness, etc., it is important to provide and maintain a continuous constant load applied as equal and opposite pure moments to each end of the test panel throughout the test cycle. However, test panels may generate a variable amount of counter-torque force against the bending force applied to it by the panel testing machine during a given test cycle. For instance, increased or decreased counteracting torque forces created by the test panel while engaged at the arm assemblies during a test cycle can lead to inconsistent load application thereto if no appropriate compensation is made immediately in the drive system in real-time, which in turn can undermine the accuracy of the test results. In the present invention, a unique combination of a linear actuation drive system with a panel testing device 100 is provided which has been found to ensure that the actuator load is maintained at a constant value by maintaining a constant rate of axial translation of an output shaft of a linear actuator. As demonstrated by data described in more detail below, the successful integration of such a drive system into a panel testing machine has been surprisingly discovered to eliminate large testing errors in terms of accuracy and repeatability observed to be associated with prior hydraulic-driven systems. The new panel testing system 100 illustrated and embodied herein is robust and relatively easy to maintain and operate over a large number of test cycles.

Referring to FIG. 1, a panel bending and testing device 10 according to the present invention is illustrated. The device 10 includes a structural frame 14 including a base portion 18 and a plurality of uprights 22 extending upwardly from the base portion 18. Mesh sections 26 extend between the uprights 22 to surround at least a portion of the device 10 and serve as debris shields in a manner described further below. A panel bending assembly 23 comprises a first bearing assembly 30 which is secured to the base portion 18 and rotatably supports a first arm assembly 38. A second bearing assembly 42 is similarly secured to the base portion 18 and rotatably supports a second arm assembly 46. A drive system 80, illustrated here as including, inter alia, an integrated actuator/motor assembly 107 (hereafter referred to occasionally as the "linear actuator"), which is used provide a controlled rate of rotational motion at the arm assemblies 38, 46 via an output shaft and coupling mechanism discussed in greater detail below. In one preferred embodiment, the integrated actuator/motor assembly 107 may combine a roller screw mechanism and integral constant torque motor such as a brushless servo electric motor. In an alternative embodiment, the actuator 107 may comprise a piezoelectric actuation device operable to provide similar functionality. A manipulator 50 is secured to the base portion 18 and is illustrated in a stowed position in FIG. 1. In the stowed position, a deflection measurement assembly 54 supported by the manipulator 50 is positioned such that a shroud 58 is between the measurement assembly 54 and the panel bending assembly 23 comprising first and second arm assemblies 38, 46 for reasons discussed further below.

Figure 2:
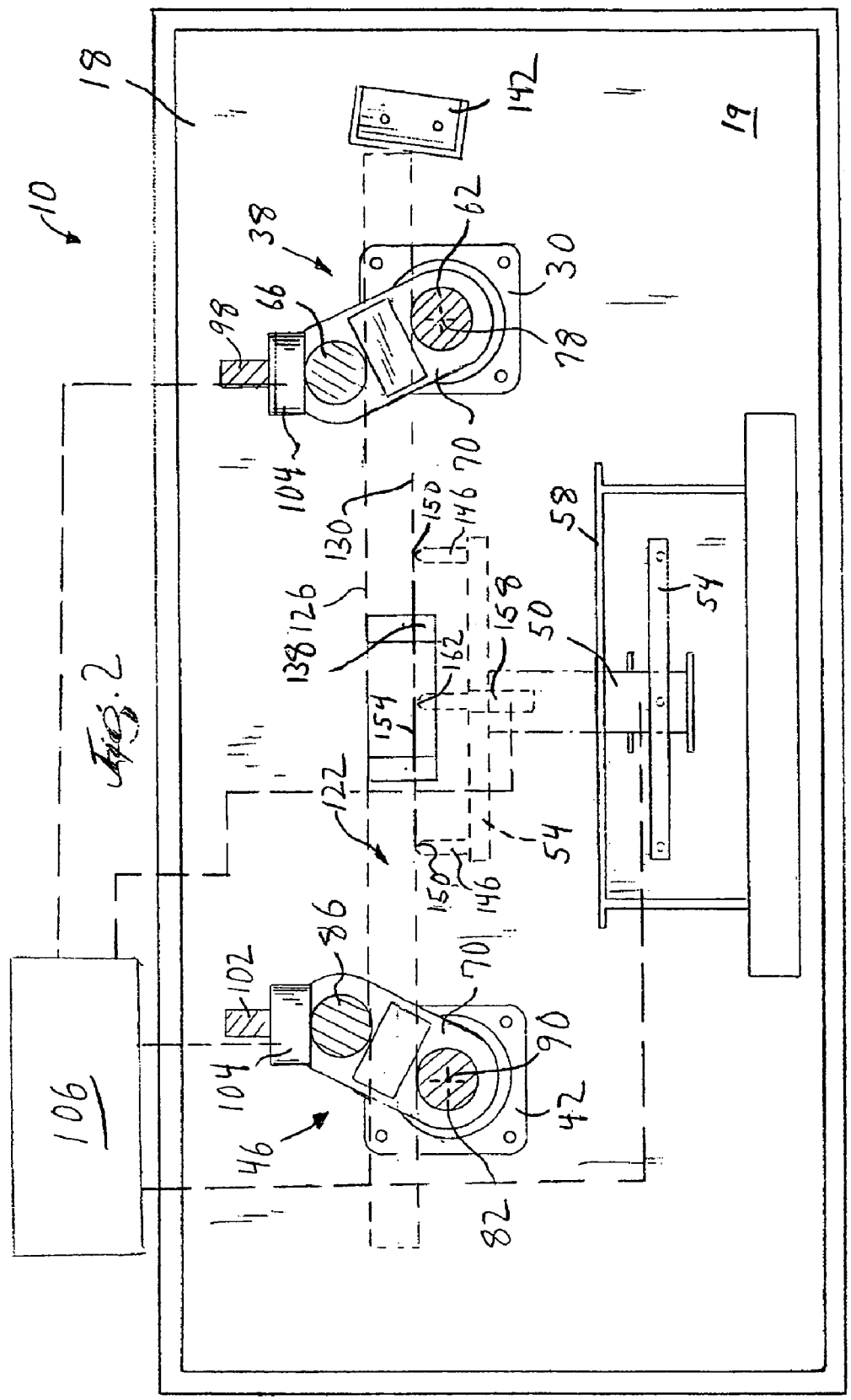
FIG. 2 is a section view taken along line 2—2 of FIG. 1.

Referring now also to FIG. 2, the first arm assembly 38 includes a first arm 62 and a second arm 66 spaced from the first arm 62. The first and second arms 62, 66 and joined to each other by a lower end plate 70, and an upper end plate 74 (see FIG. 1). A portion of the first arm assembly 38, including arm 62 but not arm 66, extends through the first bearing assembly 30 and into a space provided under a flooring portion 19 of base portion 18. The first arm assembly 38 rotates about a first axis 78 by the driven system or assembly 80 (see FIG. 3) including a linear actuator 107 located mainly outside frame 14, and a shaft component thereof (not visible in this view) that is housed within the base portion 18 which will be described further below. As illustrated, the first axis 78, about which the arm assembly 38 rotates, is substantially aligned with the first arm 62. In alternative embodiments, the first arm assembly 38 may be rotated about an axis that is not necessarily aligned with the first arm 62.

The second arm assembly 46 includes a third arm 82 and a fourth arm 86 that are also coupled to each other by lower and upper end plates 70, 74. A portion of the second arm assembly 46, including arm 82 but not arm 86, extends through the second bearing assembly 42 and into the space provided under the flooring portion 19 of base portion 18. The third and fourth arms 82, 86 are structured and configured in substantially the same way as the first and second arms 62, 66, with the exception that the third and fourth arms 82, 86 rotate about a second axis 90 in a direction opposite the first and second arms 62, 66. An upper cross-member 94 (see FIG. 1) couples the upper ends of the first and second arms assemblies 38, 46 to each other, while allowing each arm assembly to rotate about the first and second axes 78, 90, respectively. Also supported between the upper and lower end plates 74, 70 of the arm assemblies 38, 46 are reaction bars 98 and 102. The reaction bars 98, 102 are spaced from the second and fourth arms 66, 86 and each reaction bar 98, 102 supports a load sensor in the form of an axial load cell 104. One of the load cells 104 is between the reaction bar 98 and the second arm 66 and the other load cell 104 is between the reaction bar 102 and the fourth arm 86. The load cells 104 provide reaction load measurements that are subsequently used to calculate the strength and stiffness properties of the test panel. As the arms 66, 86 move toward the reaction bars 98, 102, the arms 66, 86 engage the load cells 104.

The device 10 also includes a control system 106. As illustrated, the control system 106 communicates with, among other things, the manipulator 50, the deflection measurement assembly 54, and the load cells 104. For instance, the load cells 104 are operable to generate output signals corresponding to the sensed loads at the arms 66, 86 which are communicated to the control system 106. The control system 106 is provided to control the operation of the device 10 and to record the measurements (e.g. deflection and load) that are generated during such operation, and also to monitor and control the rate of linear translation of an output shaft of the linear actuator 107 as will be described in greater detail below. The control system 106 may be in the form of a desktop computer or other types of control systems that would be suitable for use with the present invention, and will be readily apparent to those of ordinary skill in the art.

Figure 3:
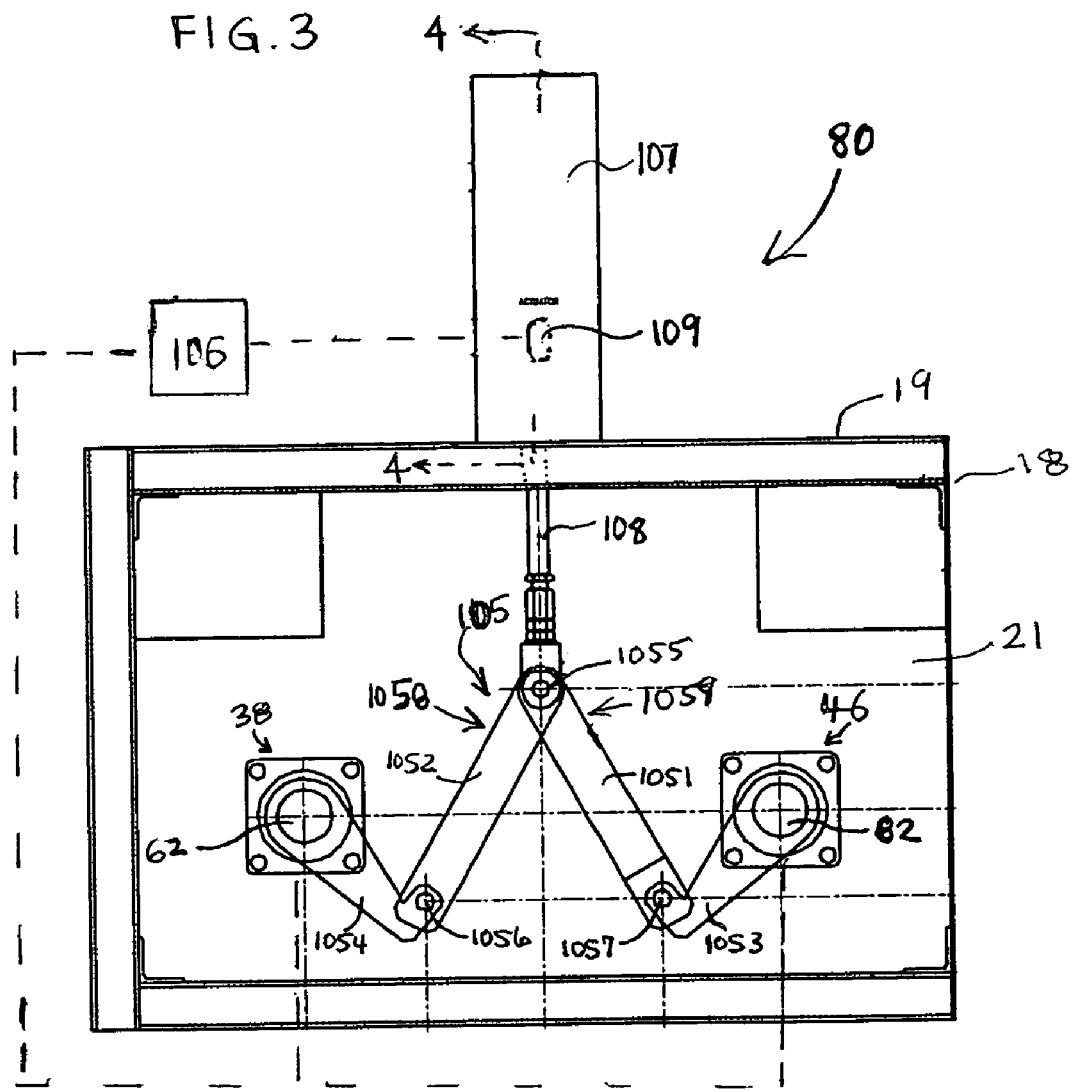
FIG. 3 is partial bottom plan view of the panel testing device of FIG. 1.

Referring to FIG. 3, the drive system 80 includes a linear actuator 107 having an output shaft 108 which is coupled to arm assemblies 38, 46 of the panel bending assembly 23 via a mechanical linkage 105 coupled to the first and third arms 62, 82, respectively. The output shaft 108 is operable to axially translate in a linear direction into and out of the space 21 provided under the flooring portion 19 of the base portion 18 of the frame 14. For instance, clearance space or a crawl space under base portion 18 or an opening through a sidewall portion of base portion 18 may be provided adequate to permit the output shaft 108 to translate in an unobstructed manner relative to the testing frame 14. The mechanical linkage 105 comprises a pair of bent levers 1058, 1059 that each are mechanically and pivotally connected at one end thereof to a distal end of the output shaft 108 of the linear actuator 107. The bent levers 1058, 1059 each include a pivot at a bent point or elbow 1056, 1057, respectively, before making a rigid, mutually pivotable connection at the opposite end thereof with a respective arm 62, 82 of the arm assemblies 38, 46 of the panel bending assembly. The mechanical linkage 105 is used to change the direction of force of the output shaft 108 by converting its linear motion to rotary motion at the respective arms 62, 82 of the arm assemblies 38, 46. In this non-limiting illustration, the mechanical linkage 105 is coupled to output shaft 108 by a clevis and pin connection 1055. The mechanical linkage 105 comprises a first levered structure 1058 and a second levered structure 1059. The first levered structure 1058 has upper arm portion 1052 and lower arm portion 1054 rotatably connected via a pin 1056. The lower arm portion 1054 is rotatably connected with arm 62. Similarly, the second levered structure 1059 has upper arm portion 1051 and lower arm portion 1053 rotatably connected via a pin 1057. The lower arm portion 1053 is rotatably connected with arm 82. In the illustrated embodiment, the mechanical linkage 105 is rigidly coupled to external circumferential portions of the first and third arms 62, 82 that extend through the bearing assemblies 30, 42, such that turning of the lower arms 1053 and 1054 in a synchronized manner via axial movement of linear actuator 107 correspondingly rotates arms 62, 82. The pair of bent levers 1058, 1059 of the mechanical linkage 105 should be machined to close tolerances during manufacture and maintained during operation to provide close similarity in part geometries and functionality therebetween to help ensure that they react essentially identically and in a synchronized manner to force inputs delivered via the output shaft 108 of the linear actuator so that the rotational movement of the arms 62, 82 is synchronized and equal in magnitude (albeit in opposite rotational directions).

In operation, the output shaft 108 of the actuator 107 extends or retracts along a linear line of motion in response to signals provided by the control system 106, thereby rotating the first and second arm assemblies 38, 46 via the mechanical linkage 105. In this illustration, the drive system 80 also includes an internal encoder 109 in linear actuator 107 that communicates with the control system 106 and is operable to instantaneously determine, at a location within the linear actuator 107, the relative axial position and compute the rate of linear motion of the output shaft 108.

For a given type of test panel, the rotational position of each arm assembly 38, 46 also may be measured directly using a suitable rotary encoder, such as an optical encoder, at test arms 62, 82, although other devices for determining the relative rotational positions of the arms 62, 82 of the arm assemblies 38, 46 also may be used, as will be readily apparent to those of ordinary skill in the art. Independent measurement of the rotational speed of the test arms 62, 82 also can provide a method of monitoring whether the load application provided by the drive system is being applied continuously at a constant rate. For instance, output signals generated by encoders at the test arms could be inputted to control system 106 controlling the rate of movement of the output shaft 108 of the linear actuator, to provide an alternative or additional feedback control scheme for managing the load application (e.g., see FIG. 3). As indicated herein, the arm assemblies 38, 46 are already in communication with the control system 106 for purposes of load sensors installed at the arm assemblies.

Figure 4:
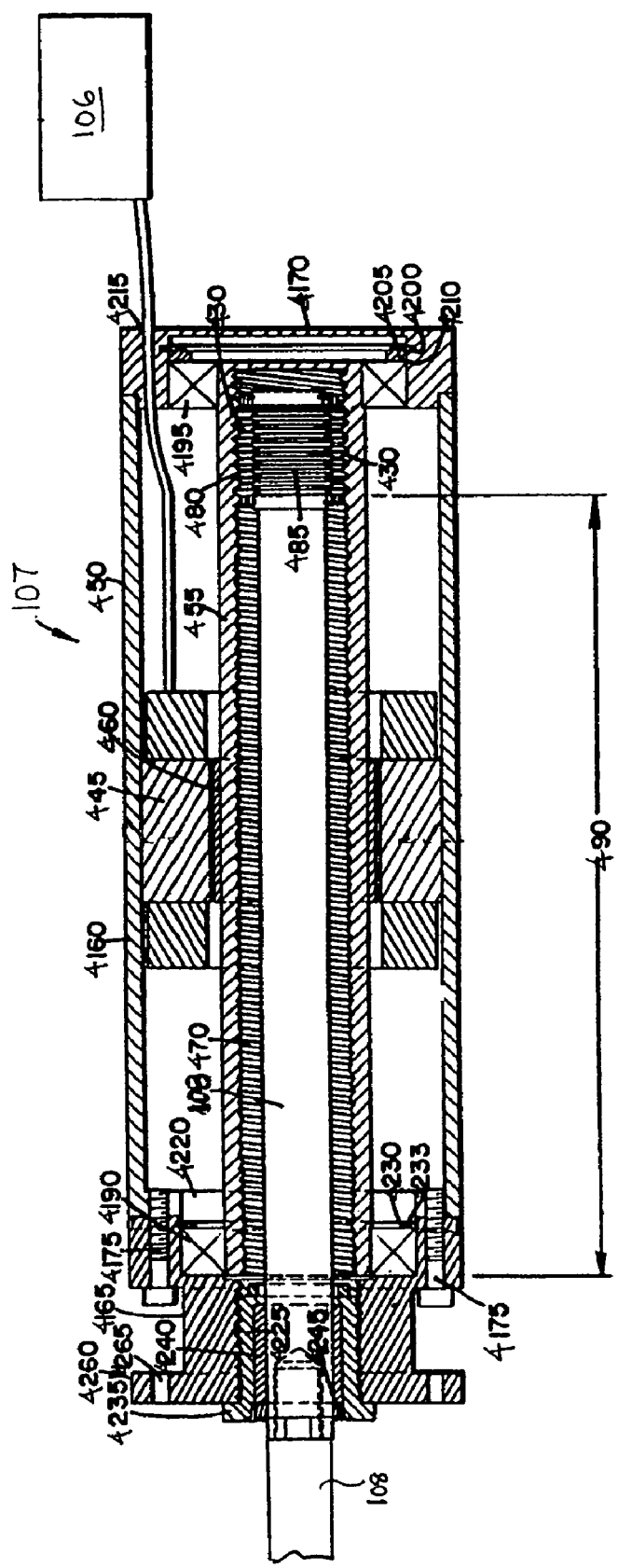
FIG. 4 is a section taken along line 4—4 of FIG. 3.

Referring to FIG. 4, linear actuator 107 is provided for converting motor power into linear motion within the actuator. Within actuator 107, multiple threaded helical transmission rollers 430, also referred to herein as planetary rollers, are assembled around the actuator's output shaft 108 and also follow threads machined on the inside surface of a hollow armature drive cylinder 455. Within actuator 107, the output shaft 108 and the armature each provided with a helical thread which mate with the threading of the planetary rollers interposed therebetween and in contact with the armature 455 and the output shaft 108. The planetary rollers convert a motor's rotary motion into linear movement of the output shaft. Roller screws which incorporate and interact with planetary rollers of this general nature have been described for non-related applications, e.g., see U.S. Pat. No. 4,648,285, which teachings are incorporated herein by reference for all purposes. A non-limiting example of a commercial actuator that can be adapted for use in the testing machine 10 according to embodiments of the present invention is an EXLAR GSX series actuator (e.g., a EXLAR GSX60 model, depending on test panel sizes), Control Techniques-Americas LLC, an Emerson Industrial Automation Company, Chanhassen, Minn.

Referring to FIG. 4 in more detail, the non-limiting illustration of linear actuator 107 includes output shaft 108, a plurality of transmission rollers 430, and an integral electric motor assembly including stator 445 and housing assembly 450. The motor assembly moves the output shaft 108 between a retracted position (shown in FIG. 4) and an extended position (not shown) and includes an elongated cylinder 455 formed of a magnetic material rotatably supported relative to the housing assembly 450. Magnets 460 are mounted about an outer surface of the cylinders 455 to form an armature with the cylinder 455 within the motor assembly. The stator 445 is attached to and supported by the housing assembly 450 and encircles the cylinder 455. An external controller 106, discussed above, selectively energizes the stator 445 to rotate the armature clockwise or counter-clockwise. The elongated cylinder 455 includes a central threaded bore 470 the threads of which are engaged by the transmission rollers 430. The output shaft 108 is coupled with the transmission rollers 430 to move along the threaded bore 470 on rotation of the cylinder 455. Only a smooth surfaced portion of the output shaft extends outside the threaded bore 470. The elongated cylinder 455 forms a drive cylinder within the actuator assembly as well as forming the armature of the motor assembly. Accordingly, the elongated cylinder 455 is referred to herein as the armature drive cylinder. The output shaft 108 and the transmission rollers 430 are axially aligned within threaded bore 470 of the armature drive cylinder 455. The rings 480 define camming surfaces which are engaged by the threaded bore 470 of armature drive cylinder 455 to move the actuator assembly along the threaded bore 470 in response to the rotation of the armature drive cylinder 455. The extent of the threaded bore 470 within the armature drive cylinder 455 defines a track along which the transmission rollers 430 of the actuator assembly move. A portion of the output shaft 108 includes annular rings 485 which are engaged by the annular rings 480 of transmission rollers 430 to advance the output shaft 108. When the armature drive cylinder 455 is selectively rotated clockwise or counterclockwise by the stator 445, the threaded bore 470 engages the annular rings 480 of the transmission rollers 430 to selectively move the rollers 430 along threaded bore 470. The annular rings 480 of the transmission rollers 430 engages the annular rings 485 of the output shaft 108 to move the output shaft 108.

The housing assembly 450 includes a cylindrical tube 460, and an end cap 465, and a circular end seal 4170. The end cap 165 is mounted to a first end of the cylindrical tube 4160 by bolts 4175 and circular end seal 4170 is mounted to a second end of the cylindrical tube 4160, as by a proper fit. The stator 445 of the motor assembly is mounted about an inner surface of the cylindrical tube 4160. The armature drive cylinder 455 is rotationally supported relative to the housing assembly 450 by front and rear bearings 4190 and 4195. The rear support bearing 4195 is mounted to an internal surface of the circular end seal 4170 to rotationally support a rear portion of the armature drive cylinder 455. The circular end seal 4170 includes a circumferential groove 4200 within which is maintained a retaining ring 4205. A bumper 4210 is interposed and held in place between the retaining ring 4205 and the bearing 4195 to absorb energy when the actuator assembly reaches the retracted position at the rear end of the threaded bore 470. The circular end seal 4170 includes a wire opening 4215 for electrically connecting the external controller 106 to the stator 445. The end cap 4165 is formed of a stepped cylindrical member having a stepped central bore defining a first bore portion 4220 and a relatively smaller diameter second bore portion 4225. The front bearing 4190 is mounted in bore portion 4220 of end cap 4165 to rotationally support a front portion of armature 455. A circumferential groove 4230 in end cap 4165 maintains retainer ring 4233 to secure bearing 4190 relative to housing assembly 450. The second bore portion 4225 is internally threaded and an externally threaded tubular bushing support 4235 is seated therein. The bushing 4240 is concentrically positioned within the bushing support 4235 to support output shaft 108 at a forward output end of the housing assembly 450. Ring seal 4245 is included at a forward end of bushing 4240. The end cap 4165 includes a flange portion 4260 having screw holes 4265 for attachment to a mounting surface, if needed. The output shaft 108 is designed to receive an extension and includes an internally threaded bore at an extended end. Other features and components of the actuator assembly include those described in U.S. Pat. No. 5,557,154, which teachings are incorporated herein by reference.

Still referring to FIG. 4, linear motion of the output shaft 108 is produced in precise synchronization with the rotation of armature 455. As will be appreciated by persons skilled in the art, the desired linear motion can be generally programmed or defined in a computer program developed by the user of the actuator entered as instructions and/or motion profiles into a programmable motion controller. The motion controller upon command may execute the user's program by signaling a servo amplifier to apply a voltage across the actuator's stator leads. The level of voltage applied is a function of the velocity specified in the user's program for the specific panel flexure test cycle being executed for a given type of structural panel. The voltage cases current to flow in the stator windings of the actuator which in turn applies a torque to the motor armature. The subsequent rotation of the armature in the actuator assembly is converted mechanically to a linear motion imparted to the actuator's output shaft. Specific instructions for the instantaneous position and velocity are transmitted by the motion controller for each flexure move executed. In response, the amplifier applies a voltage level which represents an expected velocity output of the actuator which is established by the user during setup and calibration of the system. As actual sensed velocity of the output shaft will not always match what is commanded by the motion controller, the actual movement of the actuator output shaft is monitored and appropriate adjustments are made in its velocity in real time.

To accomplish this, for example, an integral electric D.C. servo motor in the actuator supports a closed-loop servosystem in which velocity and positioning of the output shaft 108 can be closely monitored and controlled in an automated manner by the testing machine 10. For instance, a velocity/feedback sensor 109 (e.g., see FIG. 3) can be incorporated within actuator 107 by designing a servo amplifier (not shown), which can be of a conventional design used in actuators, and the controller 106 such that continuous adjustments are made to the voltage applied in response to any sensed deviation or error in position and/or velocity at the output shaft 108. Preferably, the controller 106 receives information as to the velocity and position of the actuator output shaft 108 at all times, or at highly rapid time intervals. Since the position and velocity of the output shaft 108 is a known fixed ratio of the rotation of the armature, one preferred solution is to measure its rotational position and velocity and allow the motion controller 106 to calculate the resulting position of the output shaft 108. Continual adjustment of the system command is achieved such that constant linear motion of the output shaft can be attained. Position feedback can be delivered in a variety of manners. These include resolvers, encoders or internally/externally mounted linear position feedback sensors (e.g., potentiometers, LVDTs, magnorestrictive types). A closed loop feedback control may be provided for the linear actuator 107, such as by adapting the feedback system described in U.S. Pat. No. 5,557,154, which teachings are incorporated herein by reference for all purposes. The inches of travel of the output shaft 108 during a particular testing cycle depend on the size and composition of the panel being tested and the scale of the testing machine. In general, and although not limiting, the inches of travel may range from about 2 to about 8 inches, although other distances may be encountered for different structural materials and testing machine sizes. Using this exemplary arrangement, e.g., a constant rate of linear motion of the output shaft can be provided and maintained during a testing cycle, and it generally remains within ±4.0% of a target value, particularly within ±1.0%, more particularly within ±0.5%, and most particularly within ±0.2%, during a panel testing cycle.

Figure 5:
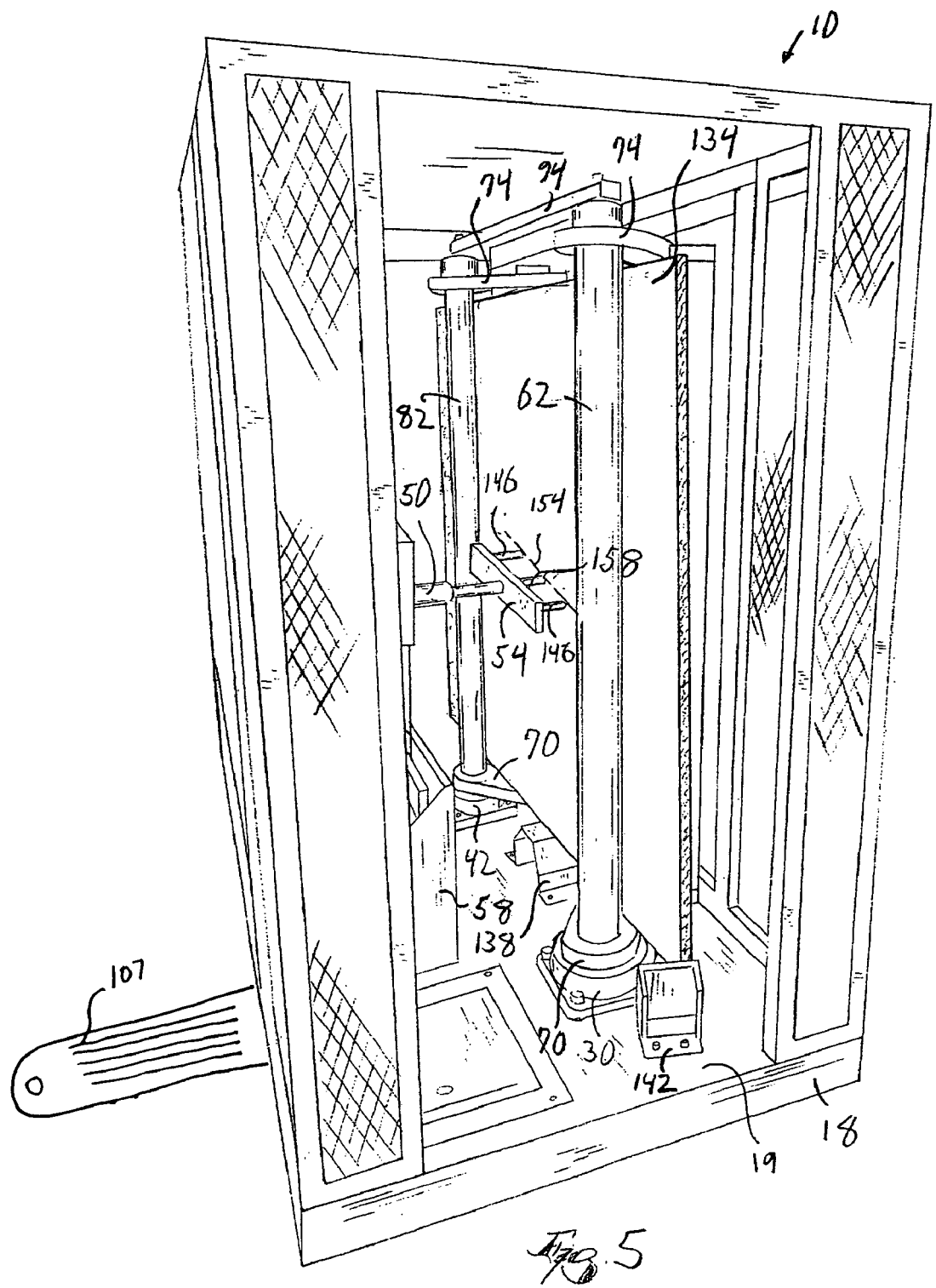
FIG. 5 is a perspective view of the panel testing device of FIG. 1 including a test panel.

Referring to FIG. 5 (and FIG. 2), a testing zone 122 is defined between an input plane 126 that is tangent to the second and fourth arms 66, 86, and an output plane 130 that is tangent to the first and third arms 62, 82. A test panel 134 is insertable into the testing zone 122 such that the panel is supported by the lower end plates 70 and a lower support bracket 138 that is secured to the base 18. The test panel 122 also abuts an end bracket 142 for proper positioning within the testing zone 118.

The deflection measurement assembly 54 is supported by the manipulator 50 and is movable between the stowed position and a test position. In the illustrated embodiment, the manipulator 50 comprises an actuator, described further below, and operates in response to signals provided by the control system 106. The deflection measurement assembly 54 includes a pair of outer panel engaging members 146 having tips 150. The outer engaging members 146 are substantially rigid and a sensing axis 154 extends through the tips 150 of the outer panel engaging members 146. As illustrated, the sensing axis 154 is generally perpendicular to the first and second axes 78, 90. The measurement assembly 54 also includes a deflection sensor 158 positioned between the outer engaging members 146 and including a sensor tip 162. The sensor tip 162 is movable with respect to the sensing axis 154 and the sensor 158 is configured to measure a deflection magnitude of the sensor tip 162 away from the sensing axis 154. However, as will be readily apparent to those of ordinary skill in the art, other types of sensors may be used in accordance with the present invention.

Referring to FIG. 2, the manipulator 50 is configured to move the deflection measurement assembly 54 between the stowed position (illustrated in solid lines) and the test position (illustrated in phantom). When the measurement assembly 54 is in the stowed position, the sensor 58 and the outer engaging members 146 are positioned behind the shroud 58 such that the sensor 158 and the members 146 are shielded from debris that may be created during device operation. When the measurement assembly 54 is in the test position, the sensor tip 162 and the tips 150 are engaged with the test panel 134. In the illustrated embodiment wherein the manipulator 50 includes an actuator 164, the manipulator 50 is configured to provide a substantially constant biasing force urging the measurement assembly 54 into engagement with the panel 134. Specifically, the manipulator 50 includes a pressure regulator 166 that is coupled to the actuator 164 and regulates the pressure within the actuator 164 during operation of the device 10. When the manipulator 50 moves the measurement assembly 54 to the test position, the actuator 164 extends or elongates, thereby engaging the member tips 150 and the sensor tip 162 with the panel. The actuator 164 is also retractable to disengage the member tips 150 and the sensor tip 162 from the panel. As the panel is bent toward the manipulator 50, the sensing axis 154 is moved toward the manipulator 50, thereby shortening the length of the actuator 164.

Figure 6:
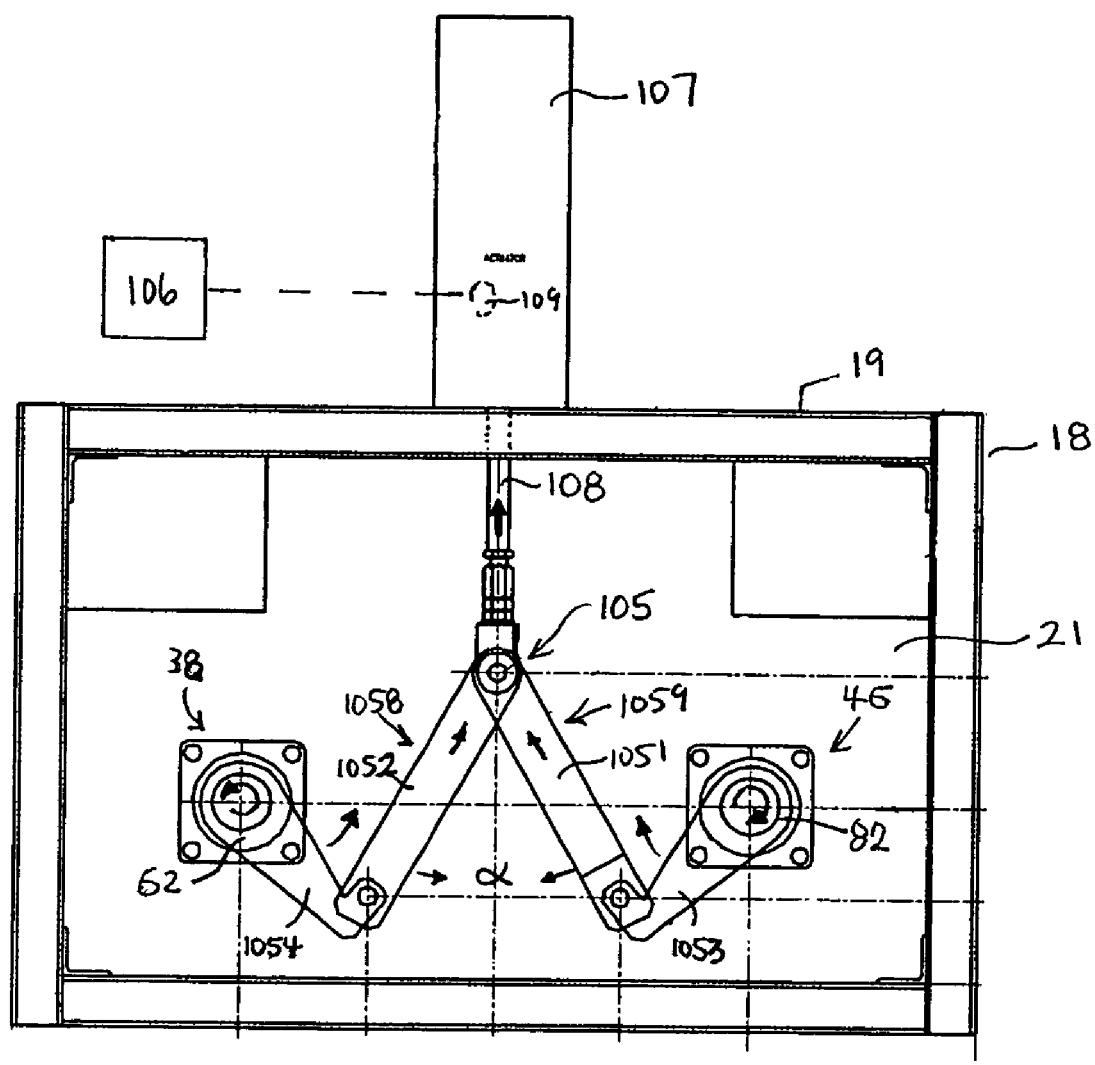
FIG. 6 is a partial bottom pan view of the panel testing device of FIG. 1, including direction arrows indicating movement of parts during a testing cycle.

Referring to FIG. 6, direction are included showing the movement of output shaft 105 of the linear actuator 107 as it is retracted to increase torque on arms 62, 82. The output shaft 105 translates axially in a linear manner, while upper arm portions 1051 and 1052 of mechanical linkage 105 (forming a Y-shape) have bi-directional movement both axially and the acute angle alpha (α) between them is reduced slightly. The associated upper arm portions 1054 and 1053 of mechanical linkage 105 pivot inward towards linear actuator 107 as indicated. This in turn induces arms 62 and 82 to rotate in opposite directions relative to each other in a synchronized manner and in directions imposing a greater bending force upon a test panel engaged by the panel bending assembly.

Figure 7:
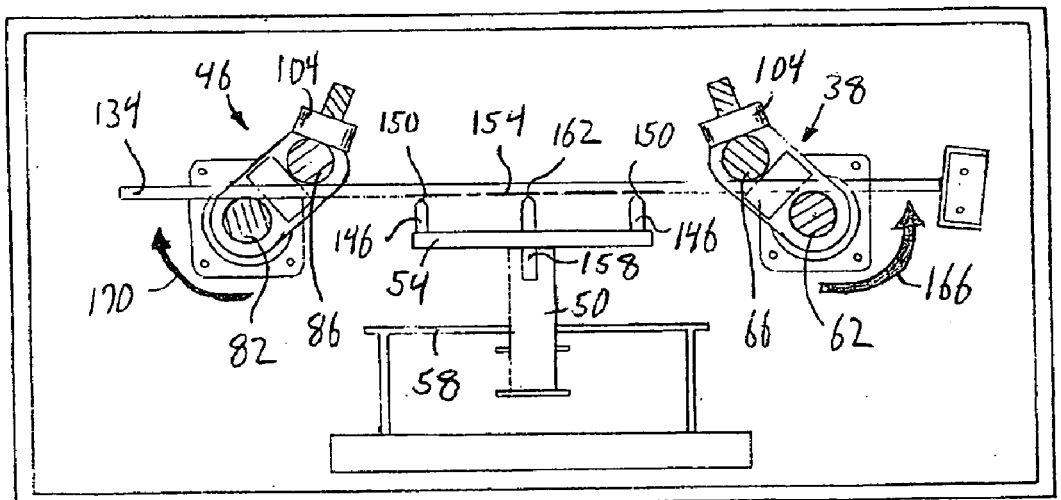
FIG. 7 is a top plan view of the panel testing device of FIG. 5 prior to a panel testing device.
Figure 8:
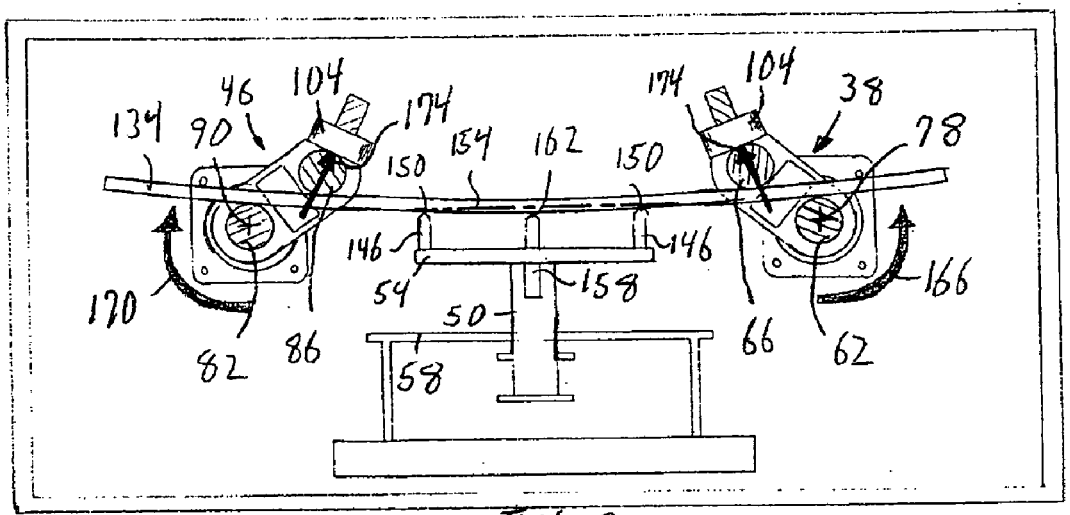
FIG. 8 is a top plan view of the panel testing device of FIG. 5 during a portion of the panel test.
Figure 9:
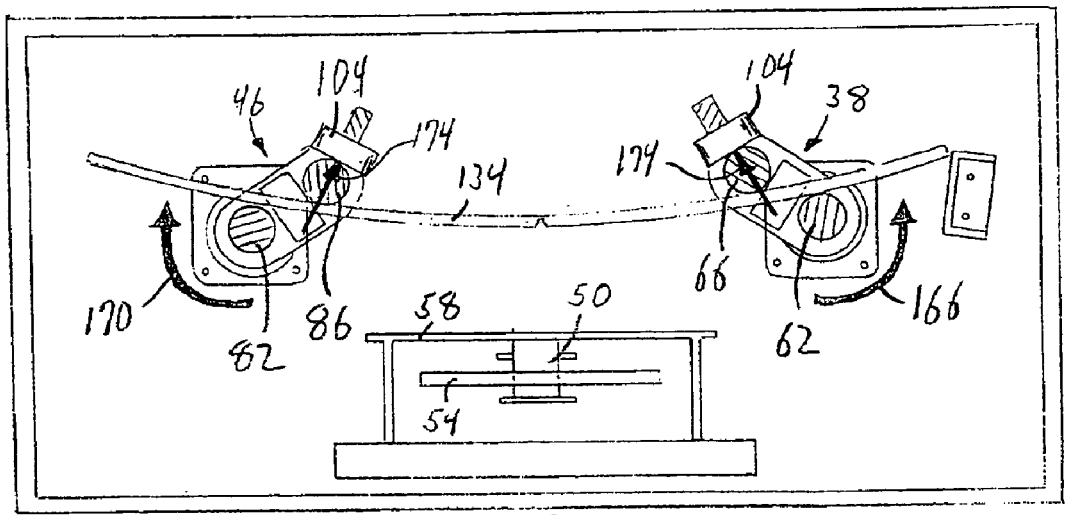
FIG. 9 is a top plan view of the panel testing device of FIG. 5 near completion of the panel test cycle.

Referring now to FIGS. 7 through 9, the operation of the device 10 through a complete test cycle is illustrated. With the test panel 134 inserted into the testing zone 122 (see FIG. 2), the control system 106 signals the actuator 107 (FIG. 3) to retract, thereby rotating the first arm assembly 38 in a counter-clockwise direction 166 and the second arm assembly 46 in a clockwise direction 170. As a result, the first and third arms 62, 82 engage one side of the test panel 134 and the second and fourth arms 66, 86 engage an opposite side of the test panel 134. As the second and fourth arms 66, 86 engage the test panel 134 the arms 66, 86 moved toward the reaction bars 98, 102 and engage the load cells 104, which subsequently send load data to the control system 106. By receiving a non-zero load reading from the load cells 104, the control system 106 is able to determine that the test panel 134 is securely engaged on each side by the arms 62, 66, 82, and 86.

During a test cycle, the linear actuator 107 is used with varying forces at a constant specified velocity. This linear actuator preferably comprises a roller screw, rolling elements, and a servo-mechanical means of powering the device, such as described above. Preferably, a D.C. servo-mechanical drive is used to maintain constant velocity. However, any other type of power transmission that supplies the desired torque at constant velocity also may be used. This may include D.C. stepper motors, constant torque AC motors, or any other type of constant velocity power transmission. In any case, the motor is given a command from controller 106 to turn a linear output shaft including a threaded portion (screw) within the actuator 107 at a constant velocity regardless of different torque required. This actuator 107 then moves the panel bending arms 62, 82 via mechanical linkage 105 that flex the test panel, which in turn allows collection of the needed data for calculating strength and stiffness of the test panel. The whole time the actuator 107 is being used, a feedback signal from a closed-loop servo system, such as described above, communicates with the drive telling the system exactly how fast the actuator is traveling and how far the actuator has traveled. It will be appreciated that the output shaft 108 of the linear actuator can be attached to the testing arms in a variety of ways. It can be attached directly to the arms, e.g., pulling them together as the screw retracts, it can be attached directly to the arms pushing them apart as the screw extends, or, as illustrated above, it can be mounted external to the arms connected to them by some mechanical means such as a set of linkage arms.

As illustrated in FIG. 7, the control system configures the arm assemblies 38, 46 such that the test panel 134 is held securely by the device 10, but is not bent or otherwise deflected. Once the panel 134 is in place, the control system 106 signals the manipulator 50, which subsequently moves the deflection measurement assembly to the test position such that the tips 150 and the sensor tip 162 engage the test panel. Note that prior to initiation of the test cycle, the sensor tip 162 is substantially aligned with the sensing axis 154.

Referring to FIG. 8, the first and second arm assemblies 38,46 are rotated about the first and second axes 78, 90, respectively by the actuator 107 such that the test panel 134 is bent or deflected about a bending axis (not shown) toward a first bent position. As the test panel 134 is bent, the second and fourth arms 66, 86 are urged toward the reaction bars 98, 102 due to resistance provided by the panel 134. The second and fourth arms 66, 86 slide within the slots 110 (shown in FIG. 3) and press against the load cells 104 such that substantially all the resistance to bending provided by the panel is counteracted by the load cells 104. In this respect, the load cells 104 are able to measure the magnitude of a bending or resisting force 174 provided by the panel 134 as the panel 134 is bent due to the rotation of the first and second arm assemblies 38, 46. Simultaneously, the sensor tip 162 is deflected away from the sensing axis 154 and the sensor 158 measures the magnitude of the deflection of the sensor tip 162. The measurements taken by both the load cells 104 and the sensor 158 are recorded by the control system 106 for further processing in order to determine the strength and stiffness of the test panel 134.

Once the panel 134 has been bent to the first bent position, the control system 106 starts the rotation of the first and second arm assemblies 38, 46 and signals the manipulator 50 to move the deflection measurement assembly 54 to the stowed position. In this respect, the pressure within the actuator 164 is reduced such that the actuator 164 retracts and is subsequently rotated toward the stowed position. Once the measurement assembly 54 is behind the shroud 58, the arm assemblies 38, 46 are further rotated and the panel 134 is further bent until it begins to fracture or crack (illustrated in FIG. 9). As the panel fractures, the load cells 104 continue to measure the resisting force provided by the panel 134. The shroud 58 protects the deflection measurement assembly 54 from any debris that is created while the panel 134 fractures, thereby preventing damage to the sensor 158. Additionally, the mesh sections 26 substantially reduce the expulsion of debris, as well as the panel 134 and broken panel portions, from the device 10. While the illustrated embodiment measures the load applied to the panel using the two load cells 104, it will be readily apparent to those of ordinary skill in the art that the load applied to the panel can be measured or otherwise detected in various ways. For example, a single load cell may be positioned within the hydraulic cylinder 107 and one of the reaction arms 108, and load applied to the panel would then be calculated using known engineering formulas. Other embodiments of the invention may include rotational torque sensors intercoupled between the reaction arms 108 and the first and third arms 62, 82. Such sensors generally measure the torque applied to the panel 134 by each arm assembly 38, 46 as the arm assemblies 38, 46 are rotated. Again, the resulting load applied to the panel 134 is calculated using known engineering equations. In addition, there are various other techniques for measuring or otherwise calculating the load applied to the panel 134 as the panel is bent, which will be readily apparent to those of ordinary skill in the art.

As described above, the control system 106 preferably controls substantially all aspects of the testing operations including operation of the drive system 80 to rotate the arm assemblies 38, 46, movement of the manipulator 50 between the stowed and test positions, and recordation of the load magnitudes measured by the load cells 104 and the deflection magnitude measured by the sensor 158. Preferably, the system 106 records the load and deflection magnitudes throughout the testing process such that the load and deflection data may be utilized to generate useful material property parameters that assist designers and engineers in the utilization of the test panel 134.

Although the actuation assembly has been exemplified above in one particular embodiment thereof, it will be appreciated that other embodiments in accordance with the invention also may be used, such as those illustrated in FIGS. 10–13.

Figure 10:
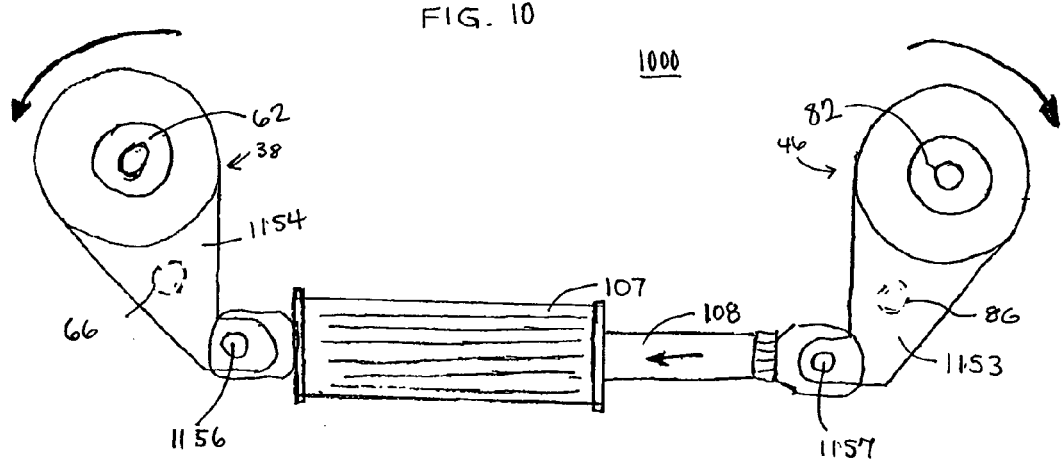
FIG. 10 is a top plan view of an actuation system for the panel testing device of FIG. 1 according to another embodiment of the invention.

In FIG. 10, an alternative actuation assembly arrangement 1000 is illustrated including a linear actuator 1070, which can be similar in construction and operation to linear actuator 107 as described above, mechanically couples arm assemblies 38, 46 via respective lever arms 1154, 1153 which are rotatably connected to arms 62, 82 for respective rotation in unison. The actuation assembly arrangement 1000 can be located in the space 21 provided below flooring portion 19 of the test frame, which was discussed above (e.g., see FIG. 3). The linear actuator 1070 may have power transmission provided via an integral constant load/torque motor run by a VFD or DC drive, such as those previously described herein, and includes a position encoder. Lever arms 1154, 1153 are similar to lever arms 1053, 1054 discussed above. Clevis and pin connections 1156, 1157 are provided to couple opposite longitudinal ends of the actuator 107 to the lever arms 1154, 1153. Other pivotal mechanical connections providing comparable function also may be used. These pivotal connections made in the various lever arms described herein can be bushed, and to the extent the parts are machined to close tolerances, minimal or no lubrication and related maintenance generally is required. The locations of the other arms 66, 86 of the arm assemblies 38, 46, which are not connected to lever arms 1154, 1153 and instead are mounted onto the base portion 18 of the testing frame 14 (FIG. 1), are indicated in broken lines. In FIG. 10, the output shaft 108 of the actuator 107 is shown as being retracted (as indicated by the direction arrow) during a loading phase of the test cycle when increasing bending load force is being applied to a test panel engaged by the panel bending device. The lever arms 1154, 1153 thusly are pulled and rotated towards each other, which in turn rotates arms 62, 82 in the indicated opposite directions. During a relief phase of a test cycle where bending forces applied to a panel are reduced or eliminated, the actuator 107 would be operated to extend output shaft 108 in the opposite linear direction effective to push the lever arms 1154, 1153 and effect a reverse direction of rotation at arms 62, 82. In general, but not necessarily for all cases, the lever arms 1154, 1153 and arms 62, 82 will be rotated through an acute angle less than 90 degrees (absolute magnitude) during either a bending or relief phase of a testing cycle. The amount of rotation experienced by these parts during a testing cycle can vary depending on variables such as the size (e.g., thickness) and composition of the test panel. For instance, a thin flexible panel may be able to tolerate a greater extent of bending (e.g., up to rupture) than a thick rigid panel, which will affect the extent of rotation of the bending arms incurred during a testing cycle phase.

Figure 11:
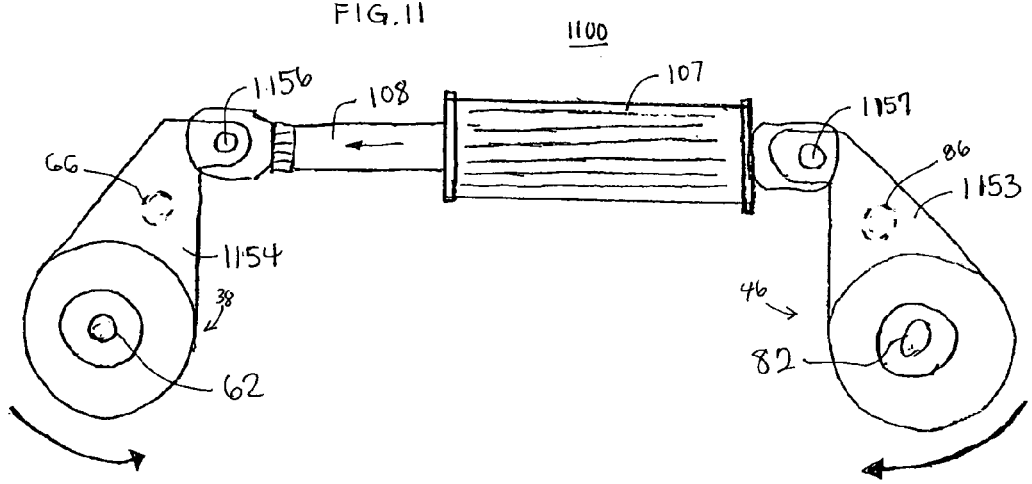
FIG. 11 is a top plan view of an actuation system for the panel testing device of FIG. 1 according to yet another embodiment of the invention.

In FIG. 11, a variation on the embodiment of FIG. 10 is shown as actuation assembly arrangement 1100 in which lever arms 1154, 1153 have been rotated 180 degrees relative to their connection to arms 62, 82. In this scenario, the actuator 1070 pushes the lever arms away from each other and rotates them in opposite directions as compared to the arrangement of FIG. 10 to receive the same end results for a load applying segment of a test cycle. That is, during a load application phase of the test cycle, output shaft 108 is extended, as indicated by the direction arrow, and it would retract in the opposite linear direction during a relief phase thereof. In other respects, the equipment arrangement, installation, and manners of operation of a panel testing device using the actuation system shown in FIG. 11 may be the same as that of FIG. 10 described above.

Figure 12:
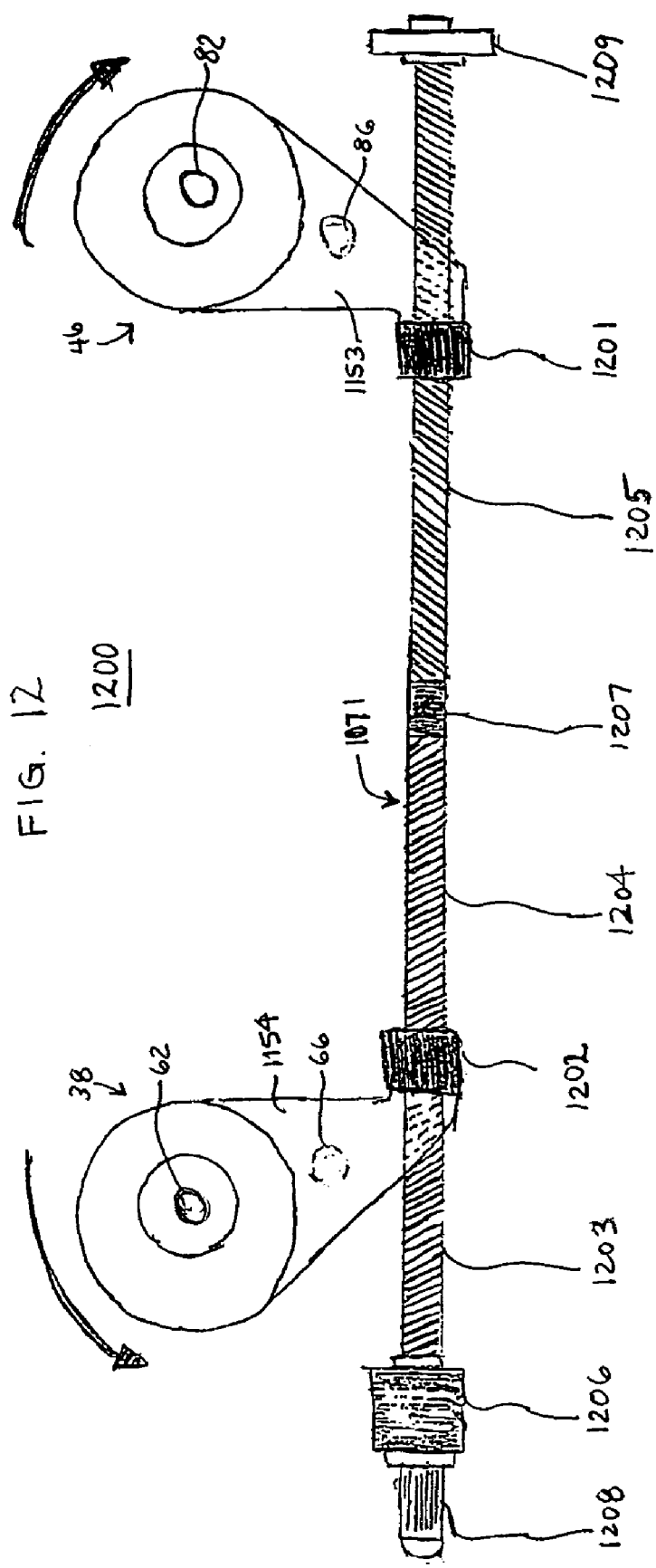
FIG. 12 is a top plan view of an actuation system for the panel testing device of FIG. 1 according to yet another embodiment of the invention.

In FIG. 12, actuation assembly arrangement 1200 has an alternative configuration in which a linear actuator 1071 includes coupler nuts 1201, 1202 which are threaded female versions of the associated segments 1204, 1205 of threaded actuator screw 1203. By mechanically fixing the coupler nuts 1201, 1202 to the arms 62, 82 via lever arms 1154, 1153, as the screw 1203 turns, the lever arms 1154, 1153 are induced to rotate which in turn rotates arms 62, 82, respectively. In order to induce arms 62, 82 to rotate in opposite directions at the same time as indicated FIG. 12, the screw 1203 has a left hand threaded portion 1204 and a right hand threaded portion 1205 (or vice versa) connected via coupling 1207 located intermediate arm assemblies 38, 46. The coupling nuts 1201, 1202 have internal threading compatible with the associated segment 1204 or 1203 of the screw 1203. The linear actuator 1071 may have power transmission provided, e.g., as an integral constant load/torque motor 1208 run by a VFD or DC drive together with gear box 1206, and includes a position encoder (not shown). An axial load bearing 1209 is provided at the opposite end of actuator

1071. During actuation of the linear actuator 1071, this arrangement allows the lever arms 1154, 1153 to be moved and rotated either towards each other or away from each other in synchronization to impart the desired directions of rotation at arms 62, 82, depending on whether a loading phase or relief phase of the test cycle is involved. FIG. 12 indicates a loading phase of the test cycle. Rotational directions of the lever arms 1154, 1153 and the associated bending arms 62, 82 will be reversed for a relief phase of a testing cycle.

In FIG. 13, actuation assembly arrangement 1300 has another alternative configuration in which a linear actuator 1072 has a power transmission provided, e.g., as an integral constant load/torque motor 1308 run by a VFD or DC drive together with gear box 1306, and includes a position encoder (not shown), and the screw has a right hand threaded portion 1304 and a left hand threaded portion 1305 (or vice versa) connected respectively to the lever arms 1154, 1153 via clevis and pin connections 1358 and 1357 such as types previously described herein or functionally comparable mechanical connections. The lever arms 1154, 1153 are in turn rotatably connected to arms 62, 82 for respective rotation in unison. This arrangement 1300 allows the lever arms 1154, 1153, and concurrently the bending arms 62, 82, to move towards each other or away from each other dependant on the rotation of the motor and gearbox. In the illustration of FIG. 13, a loading phase of the test cycle is indicated. Rotational directions of the lever arms 1154, 1153 and the associated bending arms 62, 82 will be reversed for a relief phase of a testing cycle.

Tables 1 and 2 show data representative of operational characteristics of a panel testing device 10 equipped with a closed loop feedback controlled servomotor-powered linear actuator according to an embodiment of the present invention as compared to a commercial panel bending and testing device equipped with a hydraulic actuation system. The commercial panel testing device studied was a TECO panel bending and testing device, Timerbco, Inc. d/b/a TECO, Madison Wis. The inventive panel bending and testing device was a modified version of the TECO system in which the drive system of the TECO system was removed and replaced with a drive system comprising a linear actuator, servo drive and motor (e.g., such as described above in connection with FIGS. 1–9). To acquire the data, the following common parameters were employed for non-destructive panel tests (i.e., panels were not flexed to rupture) conducted on each type of testing system: the test panels and associated test conditions were (1) 4×4 sq. ft. ADVANTECH panels (thickness=23/32 inch), eight panels each deflected three times (N); and (2) 4×4 sq. ft. ZIP Roof panels (thickness=½ inch), six panels each deflected three times (N). EI parallel ("EI para") and EI perpendicular ("EI perp") were determined for the test panels. The above-indicated test panels were commercial products obtained from Huber Engineered Woods, Commerce Ga. The Gage R&R (R %) results are reported in Table 1, and the pooled standard deviation ("pooled stdev"), R-sq adj. (%), average values (EI/ft), and average increase values are reported in Table 2.

The test panels were deflected on each type of tested equipment in accordance with the testing conditions prescribed in ASTM D 3043-95, method C, which descriptions are incorporated herein by reference.

TABLE 1

| Test panel | Thickness | Direction | Comparison Device With Hydraulic Actuator % R | Inventive Device With Linear Actuator % R |
|---|---|---|---|---|
| (1) | 23/32" | Para | 24.8 | 11.2 |
| (1) | 23/32" | Perp | 61.1 | 45.2 |
| (2) | 1/2" | Para | 26.8 | 15.0 |
| (2) | 1/2" | Perp | 18.6 | 32.1 |

TABLE 2

| Test Panel/Direction | (1)/Parallel | | (1)/Perpendicular | | (2)/Parallel | | (2)/Perpendicular | |
|---|---|---|---|---|---|---|---|---|
| Actuator | hydraulics | linear | hydraulics | linear | hydraulics | linear | hydraulics | linear |
| Pooled stdev | 6382 | 3151 | 2604 | 1881 | 2721 | 1644 | 703 | 1462 |
| R-sq adj. (%) | 93.3 | 98.6 | 60.6 | 78.1 | 92.0 | 97.4 | 96.1 | 88.5 |
| Stiffness, avg. value (EI/ft) | 373385 | 401101 | 154392 | 169302 | 121437 | 128729 | 63233 | 64709 |
| avg. % increase (stiffness) | | 7.4 | | 9.7 | | 6.1 | | 2.4 |

The repeatability tests showed that with the same non-destructive test performed on panels that the inventive panel testing system had decreased variation by up to 50%, and increased measured values by up to 10%, as compared to the comparison bending system using hydraulic actuation. The Gage R&R for the comparison bending machine ranged from 19% to 61% repeatability, depending on thickness of panel and direction of deflection. The inventive panel bending system showed major improvement: a gage R&R ranging from 11% to 45%, and average values of stiffness increasing from 2% to 10%. With the inventive panel bending system, the repeatability error was reduced on average by 25%, and was in some cases reduced by half (50%), as compared to the comparison bending machine. In addition, average values of stiffness increased by approximately 8% with the inventive bending system as compared to the comparison system using hydraulic actuation.

With respect to the comparison bending machine using a hydraulic actuator system, it was visually observed during the panel tests that the actuator output shaft noticeably paused or hesitated, then lurched forward and did not extend at a smooth constant rate during initial loading of a panel at low test load conditions, which significantly contributed to measurement error. These undesired effects did not occur on the inventive panel bending machine under comparable test conditions (i.e., other than the noted equipment design differences that existed therebetween).

Although not desiring to be bound to any particular theory, it is thought that in the inventive system the servomotor can continuously provide a constant rate of linear motion of the linear actuation during a panel test cycle that eliminates error associated with the prior hydraulic system, which in turn provides more accurate results. With the reduction in error, not only does repeatability improve, but average values increased significantly. This can result in large savings in manufacturing as production can utilize fewer raw materials to meet specifications. The linear actuator and motor are easy to use and accurate, and are capable of handling many different panel sizes and need minimal calibration checks.

Moreover, as indicated, it was observed in these experiments that the hydraulic actuator did not maintain a constant velocity, and, especially under low pressure (i.e., low load) conditions, had the tendency to pause, and "surge" or "lurch forward" which significantly added to measurement error. In addition, the hydraulics were observed to behave differently as the fluid heated up with prolonged use of the device where no "rest" or cooling period is provided. Also, the hydraulic fluids have been observed to be susceptible to changes in performance behavior depending on the ambient temperature of the environment in which the panel bending machine using such a hydraulic system is installed. As such panel bending devices may be installed outdoors, the ambient temperature can deviate significantly, depending on the climate in which the device is installed, which represents a drawback for the hydraulic-actuated systems. As results are calculated from the movement of the sample in coordination with the applied load, any movement error or measurement error artificially lowers the result, and the variation in testing one sample (non-destructively) multiple times was observed to be very high for the comparison system using hydraulic actuation. These studies and observations revealed that the hydraulic-pneumatic system is extremely variable, especially at forces less than 200 pounds, which leads to highly variable results. This is believed due in part to the internal components of a hydraulic cylinder or motor such as the seals. These seals are designed to keep dust, debris, and any foreign particulate out of the hydraulic system while keeping the oil inside. It is theorized that the inherent problem when using a hydraulic system in a process of this sort is that these seals provide a resistance to the system and especially under low pressures, these seals will resist movement until the system builds enough pressure to overcome this resistance. Once this resistance has been overcome, the cylinder will surge or shoot forward at a rapid rate until the servo valve compensates for the sudden movement, and the time it takes to compensate is built in error. With the inventive panel testing device, the output shaft is moving at a constant velocity regardless of the torque required. The stroke of the comparison system using hydraulics, and the torque it could apply, limits the types of products that can be run on the system. In contrast, the inventive bending machine makes it possible to pivot the panel bending arms through greater rotational distances, thus allowing thinner panels to be tested on the device. It also becomes possible to supply more torque to the testing arms, thus allowing thicker panels to be tested.

While the invention has been particularly described with specific reference to particular process and product embodiments, it will be appreciated that various alterations, modifications and adaptations may be based on the present disclosure, and are intended to be within the spirit and scope of the present invention as defined by the following claims.

What is claimed is:

1. A panel testing device for flexing and measuring mechanical properties of a panel, comprising:
    a panel bending assembly operable to engage a panel and impart a bending force on the engaged panel;
    a linear actuator having an output shaft coupled to the panel bending assembly, wherein the linear actuator converts rotary motion into linear movement of the output shaft, and wherein the output shaft is operable to be movable relative to the panel bending assembly where movement of the output shaft correspondingly changes a bending force applied to a test panel engaged by the panel bending assembly;
    a position feedback assembly operable to generate signals corresponding to the position and velocity of the output shaft of the linear actuator;
    a deflection measurement assembly operable to measure a deflection of the panel; and
    a control system communicating with the linear actuator and the deflection measurement assembly for controlled operation thereof including receiving first signals from the deflection measurement assembly that correspond to the deflection of the panel and second signals from the position feedback assembly that correspond to the position and velocity of the output shaft of the linear actuator, wherein the control system is adapted to adjust the velocity of the output shaft in response to the second signals.

2. The panel testing device of claim 1, wherein the control system is adapted to adjust the velocity of the output shaft in response to the second signals to produce continuous motion and a constant rate of linear motion thereof regardless of torque resisting such motion at the panel testing assembly.

3. The panel testing device of claim 1, wherein the output shaft is coupled to the panel bending assembly via a mechanical linkage.

4. The panel testing device of claim 1, wherein the linear actuator comprises a roller screw and rolling elements operably connected to a rotary power transmission source and the output shaft.

5. The panel testing device of claim 4, wherein the linear actuator comprises multiple threaded helical rollers assembled in a planetary arrangement around a portion of the output shaft comprising a threaded shaft, wherein the linear actuator converts rotary motion into linear movement of the threaded shaft.

6. The panel testing device of claim 1, further comprising a closed loop D.C. servomotor operable to power the linear actuator.

7. The panel testing device of claim 1, further comprising a constant power transmission to power the linear actuator selected from the group consisting of a D.C. servomotor, a D.C. stepper motor, and a constant torque A.C. motor.

8. The panel testing device of claim 1, wherein the position feedback assembly is selected from the group consisting of a resolver, a linear position feedback sensor, and an encoder.

9. The panel testing device of claim 1, wherein the deflection measurement assembly comprises an end portion supporting a deflection sensor, wherein the end portion being movable between a non-testing position where the deflection sensor is out of contact with the panel and a test position where the sensor is in contact with the panel when the deflection sensor is in the test position operable to measure a deflection of the panel.

10. The panel testing device of claim 1, further comprising
a frame;
the panel bending assembly further comprising:
a first arm assembly pivotally mounted to the frame and including a first arm engageable with a first major face of the panel and having a generally perpendicular first axis, and second arm engageable with a second major face of the panel and having a generally perpendicular second axis that is spaced from and substantially parallel to the first axis,
a second arm assembly pivotally mounted to the frame and including a third arm engageable with the first major face of the panel and having a generally perpendicular third axis, and fourth arm engageable with the second major face of the panel and having a generally perpendicular fourth axis that is spaced from and substantially parallel to the third axis, wherein the first and third arms being controllably pivotable in opposing rotational directions to bend the panel via external mounts made thereto with the linear actuator,
wherein the linear actuator is operable to simultaneously pivot the first and third arms in opposite rotational directions at essentially the same rotational speeds.

11. The panel testing device of claim 10, wherein the output shaft of the linear actuator is coupled to the first and third arms via a mechanical linkage.

12. The panel testing device of claim 11, wherein the mechanical linkage comprises a pair of bent levers each of which are mechanically and pivotally connected at one end thereof to a distal end of the output shaft of the linear actuator, and the bent levers each include a pivot at an elbow thereof, respectively, before making a rigid, mutually pivotal connection at the opposite end thereof with a respective first or third arm of the respective first or second arm assemblies.

13. The panel testing device of claim 11, wherein the mechanical linkage comprises first and second lever arms connected to (i) the linear actuator, which includes a threaded drive screw, and (ii) the first and third arms, respectively, in a rotatable manner, wherein the linear actuator is operable to simultaneously rotate the first and second lever arms in equal and opposite rotational directions thereof in response to linear translation of the threaded drive screw.

14. The panel testing device of claim 11, wherein the mechanical linkage comprises first and second lever arms connected to (i) the first and third arms, respectively, in a rotatable manner, and (ii) the linear actuator, wherein the linear actuator includes a threaded drive screw, and first and second internally-threaded coupler nuts coupling the threaded drive screw to the respective first and second lever arms, and wherein the threaded drive screw is comprised of a left hand threaded portion and a right hand threaded portion each mechanically coupled with either of the first or second coupling nuts having corresponding internal threading, wherein the linear actuator is operable to simultaneously rotate the first and second lever arms in equal and opposite rotational directions thereof.

15. The panel testing device of claim 11, wherein the mechanical linkage comprises first and second lever arms connected to (i) the first and third arms, respectively, in a rotatable manner, and (ii) the linear actuator, wherein the linear actuator includes a threaded drive screw, wherein the threaded drive screw is comprised of a left hand threaded portion and a right hand threaded portion each mechanically coupled at one respective end portion thereof with either of the first or second lever arms and at an opposite end portion thereof are commonly driven by the same power transmission means, wherein the linear actuator is operable to simultaneously rotate the first and second lever arms in equal and opposite rotational directions thereof.

16. The panel testing device of claim 10, wherein the linear actuator comprises first and second linear actuator assemblies each coupled via a respective lever arm at a respective output shaft thereof to the first and third arms of the panel bending assembly, and the first and second linear actuator assemblies commonly controlled by the control system to operate in synchronization.

17. The panel testing device of claim 1, further comprising a load sensor engaging at least one of the arms, wherein the load sensor measures at least a portion of a bending load that is applied to the panel as the arm assembly pivots.

18. A method for testing a panel of material, comprising:
(A) providing a panel testing device configured to flex a test panel comprising
a panel bending assembly operable to engage a panel and impart a bending force on the engaged panel;
a linear actuator having an output shaft coupled to the panel bending assembly, wherein the linear actuator converts rotary motion into linear movement of the output shaft, and wherein the output shaft is operable to be movable relative to the panel bending assembly where movement of the output shaft correspondingly changes a bending force applied to a test panel engaged by the panel bending assembly;
a position feedback assembly operable to generate signals corresponding to the position and velocity of the output shaft of the linear actuator;
a deflection measurement assembly operable to measure a deflection of the panel; and
a control system communicating with the linear actuator and the deflection measurement assembly for controlled operation thereof including receiving first signals from the deflection measurement assembly that correspond to the deflection of the panel and second signals from the position feedback assembly that correspond to the position of the output shaft of the linear actuator, wherein the control system is adapted to adjust the velocity of the output shaft in response to the second signals;
(B) inserting a test panel into the testing device;
(C) powering the linear actuator effective to impart a bending force on the test panel from opposite ends thereof;
(D) moving the output shaft at a generally constant rate along a plurality of different axial positions relative to the panel bending assembly;
(E) operating, during step (D), the deflection measurement assembly to measure the deflection of the test panel at said different axial positions and outputting signals corresponding to the amount of deflection thereof at said respective different axial positions.

19. The method of claim 18, wherein the control system adjusts the velocity of the output shaft in response to the second signals to produce continuous motion and a constant rate of linear motion thereof regardless of torque resisting such motion at the panel testing assembly.

20. The method of claim 18, further comprising bending the test panel to rupture thereof.

21. The method of claim 18, comprising measuring panel deflection in accordance with ASTM D 3043-95, method C.

* * * * *